United States Patent
Hirohara et al.

(10) Patent No.: US 7,219,999 B2
(45) Date of Patent: May 22, 2007

(54) DEVICE FOR MEASURING OPTICAL CHARACTERISTIC OF EYE

(75) Inventors: Yoko Hirohara, Tokyo (JP); Toshifumi Mihashi, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 534 days.

(21) Appl. No.: 10/494,722

(22) PCT Filed: Oct. 11, 2002

(86) PCT No.: PCT/JP02/10603

§ 371 (c)(1),
(2), (4) Date: Jun. 7, 2004

(87) PCT Pub. No.: WO03/039357

PCT Pub. Date: May 15, 2003

(65) Prior Publication Data

US 2005/0134798 A1 Jun. 23, 2005

(30) Foreign Application Priority Data

Nov. 9, 2001 (JP) .............................. 2001-345155

(51) Int. Cl.
*A61B 3/10* (2006.01)
*A61B 3/00* (2006.01)

(52) U.S. Cl. ........................................ 351/221; 351/200

(58) Field of Classification Search ........ 359/200–208, 359/211, 212, 221–223, 243
See application file for complete search history.

(56) References Cited

U.S. PATENT DOCUMENTS 6,525,883 B2 * 2/2003 Hirohara et al. ............ 359/618

FOREIGN PATENT DOCUMENTS

| JP | 10-216092 A | 8/1998 |
| JP | 10-305013 A | 11/1998 |
| JP | 11-137522 A | 5/1999 |
| JP | 2001-204690 A | 7/2001 |

* cited by examiner

*Primary Examiner*—Hung Xuan Dang
*Assistant Examiner*—M. Hasan
(74) *Attorney, Agent, or Firm*—Foley & Lardner LLP

(57) ABSTRACT

The position of an object surface is detected with an error reduced on a reflectance boundary surface. A first light source (100) emits the luminous flux of the first wavelength. A first illumination optical system (200A) illuminates a small area on a retina (61) to be examined by the first luminous flux from the first light source (100). A first reception optical system (300A) guides a part of the luminous flux which is reflected by and returning from the retina (61) to be examined to a first light reception part (510) via a first conversion member (400) for converting the reflected luminous flux into at least 17 beams. A second light source (110) emits the luminous flux of the second wavelength. A second illumination optical system (200B) illuminates a predetermined area on the retina (61) to be examined by the second luminous flux from the second light source (110). A second reception optical system (300B) guides the second luminous flux reflected by and returning from the retina (61) to a second light reception part (520). A display part checks at which position on the fundus oculi (61) of the eye (60) the luminous flux for measurement is converged or fixed, and the position of convergence and the position of measurement are changed by using a drive unit to move a fixation mark or the irradiation position of the irradiation light for Hartmann measurement.

13 Claims, 12 Drawing Sheets

(a)

(b)

DEVICE FOR MEASURING OPTICAL CHARACTERISTIC OF EYE

TECHNICAL FIELD

The present invention relates to a device for measuring an optical characteristic of an eye, and particularly to a device for measuring an optical characteristic of an eye, which irradiates a fundus of an eye to be examined with a luminous flux and measures the optical characteristic of the eye by reflected light therefrom.

BACKGROUND OF THE INVENTION

As a conventional corneal shape measuring device, there is known a device which projects a mark, obtains an imaging position of the mark, and measures a corneal shape. Besides, as a device for measuring an optical characteristic of an eye, there is a device for which the present applicant filed patent application and in which focus adjustment of an illumination optical system is performed according to the level of received light of a first light receiving part, and focus adjustment of a light receiving optical system is performed on the basis of an optical characteristic (S) obtained from the output of the first light receiving part (Japanese Patent Application No. 9-137630).

SUMMARY OF THE INVENTION

In the conventional device for measuring the optical characteristic of the eye to be examined, it was impossible to confirm to which position on the fundus the measurement luminous flux is irradiated. Thus, there also occurs a case where the measurement is performed while the fixation is insufficient, and there has occurred a request to confirm to which position on the fundus the measurement luminous flux is irradiated.

The present invention has been made in view of the above circumstances and has an object to provide a device for measuring an optical characteristic of an eye in which it is possible to confirm at which position on a fundus of an eye to be examined a luminous flux for measurement is converged or fixed, and a fixation target or an irradiation position of irradiation light for Wavefront sensing using Shack-Hartmann method is moved so that the position of convergence and the position of measurement can be changed, and the reliability of data is further raised.

According to the invention, a device for measuring an optical characteristic of an eye includes a first light source for emitting a luminous flux of a first wavelength, a first illumination optical system for performing illumination by a first illumination luminous flux which is from the first light source and is converged to a vicinity of a center of a fundus of an eye to be examined, a second light source for emitting a luminous flux of a second wavelength, a second illumination optical system for illuminating an observation area of the fundus of the eye to be examined by a second illumination luminous flux from the second light source, a beam splitter for branching a reflected luminous flux reflected from the fundus of the eye to be examined into a first branch luminous flux containing most of the reflected luminous flux of the first wavelength and a second branch luminous flux containing a remaining portion of the reflected luminous flux of the first wavelength and the reflected luminous flux of the second wavelength, a first reception optical system for receiving the first branch luminous flux branched by the beam splitter and for guiding the first branch luminous flux so as to be received through a first conversion member for converting it into at least 17 beams, a first light receiving part for receiving the first branch luminous flux from the first reception optical system, a second reception optical system for guiding the second branch luminous flux branched by the beam splitter so as to be received, a second light receiving part for receiving the second branch luminous flux from the second reception optical system, an arithmetic part for obtaining an optical characteristic of the eye to be examined on the basis of an inclination angle of the luminous flux obtained by the first light receiving part, and a display part for enabling confirmation of an irradiation position of the first illumination luminous flux on the fundus by a signal from the second light receiving part.

Some features of the embodiment will be exemplified below.

In order to know a converging point of the measurement light on the fundus, an optical system which enables observation of the fundus is provided. Besides, the fixation or the measurement light is moved so that the measurement light is converged on a specified position on the fundus and an incident position is changed.

In this embodiment, a wavelength of a fundus observation system and a measurement wavelength are slightly changed. For example, fundus illumination is made to have 860 nm, and a measurement wavelength of a Hartmann plate is made 840 nm. Then, at a light path dividing place of a measurement system, a beam splitter is put which transmits, for example, light of 860 nm, transmits 5% of light of 840 nm and reflects 95% thereof. These values are merely examples, and can be suitably changed.

A projection of the fundus observation system is made, for example, a ring-shaped or circular projection, and reflection by a cornea or a half way corneal vertex and reflection of a vertex of an optical lens are prevented. Besides, the light source is conjugated with a pupil position.

Methods of moving projection light on the fundus include two methods, that is, a method of moving the fixation, and a method of moving illumination light for eye optical characteristic measurement.

In the case where the illumination light for eye optical characteristic measurement is moved, galvanometer mirrors are put at two places, and the mirrors are respectively inclined in an x direction and a y direction, so that the incident position is changed. When a desired incident position is obtained, swing is made there in a minute angle, and uneven reflection due to disturbance on the retina is removed.

DETAILED DESCRIPTION OF PREFERRED EMBODIMENTS OF THE INVENTION

1. Optical System (First Embodiment)

Hereinafter, an embodiment of the present invention will be described in detail with reference to the drawings.

Figure 1:
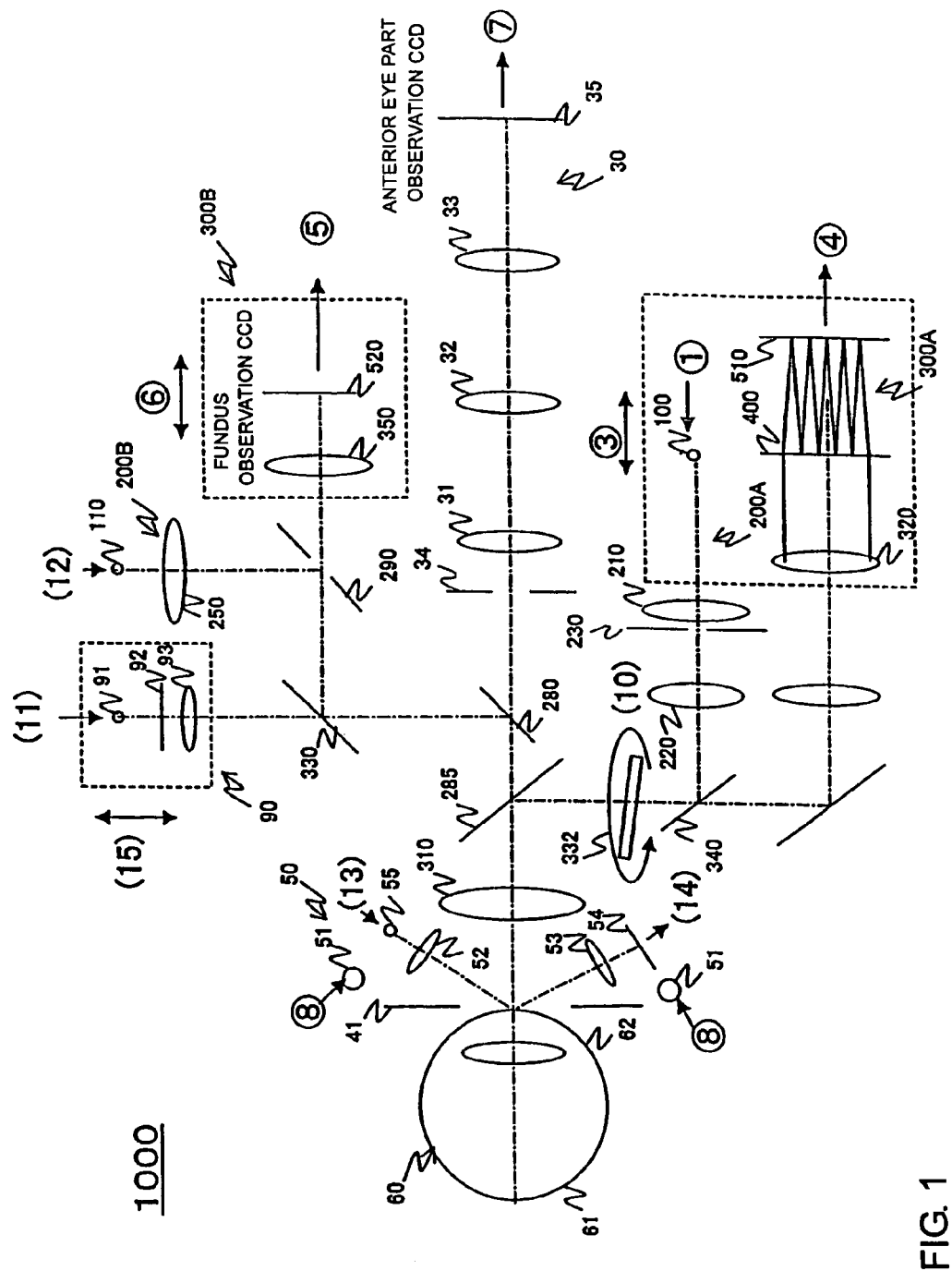
FIG. 1 is a view showing a schematic optical system of an eye characteristic measuring device 1000 of a first embodiment of the invention.

FIG. 1 is a view showing a schematic optical system of an eye characteristic measuring device 1000 of a first embodiment of the invention.

The eye characteristic measuring device 1000 includes, for example, a first light source part 100, a first illumination optical system 200A, a first reception optical system 300A, a first light receiving part 510, a second light source part 110, a second illumination optical system 200B, a second reception optical system 300B, a second light receiving part 520, a third light source part 91, a third reception optical system 30, a first adjusting optical system 50, and a third illumination optical system 90. Incidentally, with respect to an eye 60 to be examined, a retina (fundus) 61 and a cornea (anterior eye part) 62 are shown in the drawing.

The first light source part 100 emits a luminous flux of a first wavelength. The first illumination optical system 200A illuminates a minute area on the retina 61 of the eye to be examined by the first luminous flux from the first light source part 100. The first reception optical system 300A guides, for example, a part of the luminous flux reflected by and returning from the retina 61 of the eye to be examined to the first light receiving part 510 through a first conversion member 400 for converting the reflected luminous flux into at least 17 beams. The second light source part 110 emits a luminous flux of a second wavelength. The second illumination optical system 200B illuminates a specified area on the retina 61 of the eye to be examined by the second luminous flux from the second light source part 110. The second reception optical system 300B guides the second luminous flux reflected by and returning from the retina 61 of the eye to be examined to the second light receiving part 520.

Hereinafter, the respective parts will be described in detail.

The first illumination optical system 200A is for illuminating, for example, the minute area on the retina 61 of the eye to be examined by the luminous flux from the first light source part 100. The first illumination optical system 200A includes a first converging lens 210, a first relay lens 220 and a lens stop 230.

It is desirable that the first light source part 100 has high spatial coherence and not high temporal coherence. Here, as an example, an SLD is adopted as the first light source part 100, and a point light source with high brightness can be obtained. Incidentally, the first light source part 100 is not limited to the SLD, and even if both the spatial and temporal coherences are high like a laser, it can be used by inserting a rotation diffused plate or the like to suitably lower the temporal coherence. Then, even if both the spatial and temporal coherences are not high like the LED, if only the quantity of light is sufficient, it can be used by inserting a pinhole or the like at a position of a light source in an optical path. Besides, as the wavelength of the first light source part 100 for illumination, for example, a wavelength in an infrared range, for example, 780 nm can be used. In the case where the first light source part 100 is continuously turned on, the luminous flux for optical characteristic measurement and the luminous flux of the anterior eye part 62 of the eye to be examined as an object to be examined are simultaneously received by the first light receiving part 510.

The first reception optical system 300A is for receiving, for example, the luminous flux reflected by and returning from the retina 62 of the eye to be examined through a second beam splitter 340 and for guiding it to the first light receiving part 510. The first reception optical system 300A includes a first a focal lens 310, a second relay lens 320, the second beam splitter 340, and the conversion member 400 for converting the reflected luminous flux into at least 17 beams.

The conversion member 400 disposed in the first reception optical system 300A is a wavefront conversion member for converting the reflected luminous flux into plural beams. Incidentally, here, plural micro-Fresnel lenses disposed on a plane orthogonal to the optical axis are adopted as the conversion member 400.

The first light receiving part 510 is for receiving the light having passed through the conversion member 400 and from the first reception optical system 300A and for generating a first signal. With respect to the first light receiving part 510, the first light source part 100 and the fundus 61 are conjugated with each other, and the fundus 61 and the first light receiving part 510 are conjugated with each other. Further, the lens stop 230, the conversion member 400 and the pupil are also conjugated with one another. That is, the front focal point of the first a focal lens 310 is substantially coincident with the anterior eye part 62 of the eye 60 to be examined as the object to be examined. The reflected light from the fundus 62 passes through the first a focal lens 310 and the relay lens 320, and is converged on the first light receiving part 510 through the conversion member 400.

Then, the first illumination optical system 200A and the first reception optical system 300A are moved in synchronization with each other, while on the assumption that the luminous flux from the first light source part 100 is reflected at a converged point, such a relation that the signal peak at the first light receiving part 510 by the reflected light becomes maximum is kept, and they are moved in a direction in which the signal peak at the first light receiving part 510 becomes high, and are stopped at the position where the intensity becomes maximum. As a result, the luminous flux from the first light source part 100 is converged on the eye 60 to be examined.

The second illumination optical system 200B is for illuminating a specified area on the retina of the eye to be examined by the second luminous flux from the second light source part 110. The second light source part 110 is for emitting the luminous flux of the second wavelength of, for example, 860 nm. The second light source part 110 is a point light source or a surface light source to the fundus 61 and can be made to have a near-infrared region. When the wavelength of the first light source part 100 for Wavefront sensing using Shack-Hartmann method is 840 nm, and the wavelength of the light source part for the anterior eye part illumination is 940 nm, infrared or near-infrared light other than those, for example, a suitable wavelength of 850 to 930 nm (at present, for example, 860 to 880 nm) between them can be selected. The second illumination optical system 200B includes, for example, the second light source part 110, a fourth converging lens 250, and a mirror 290 with a hole. With respect to the illumination of the fundus 61, in this example, the illumination light for an observation area of the fundus 61 is formed using the mirror 290 with the hole. The center of the ring-shaped lens stop transmits 100% of light, the transmittance of its periphery is made, for example, about 10%, and the periphery illuminates the whole of the fundus. The second light source part 110 is conjugated with the pupil (imaged on the pupil), and most of the fundus is wholly and uniformly illuminated by this. Besides, the mirror 290 with the hole has a conjugated relation with the pupil so as to prevent the reflection at the corneal vertex. In the second reception optical system 300B and the second light receiving part 520, it is possible to observe the converging point on the fundus by the first light source part 100, and both the observation system by the second light source part 110 and the fixation target by the third light source part 91.

The second reception optical system 300B includes, for example, the first a focal lens 310, a first beam splitter 330, the mirror 290 with the hole, and a second converging lens 350. The light of the second wavelength reflected by a beam splitter 280 formed between the first beam splitter 330 and a beam splitter 285 is guided to the second light receiving part 520 through the first beam splitter 330 and the second converging lens 350. The second light receiving part 520 generates a second signal. The beam splitter 285 is constructed by, for example, a dichroic mirror which reflects the luminous flux of the first wavelength and transmits the luminous flux of the second wavelength. The second light receiving part 520 for receiving a formed fundus image is constructed of a light receiving element having sensitivity to infrared light. Besides, a rotary prism 332 for making the light uniform is disposed between the second beam splitter 340 and the beam splitter 285. The rotary prism 332 is conjugated with the pupil.

The third reception optical system 30 includes relay lenses 31, 32 and 33, a telecentric stop 34, and a third light receiving part (here, for example, an anterior eye part observation CCD) 35. The third reception optical system 30 guides a luminous flux, which is formed such that a pattern of a Placido's disk 41 illuminated from a light source part included in the first adjusting optical system 50 is reflected by and returns from the anterior eye part 62 of the eye 60 to be examined, to the third light receiving part 35. Besides, the telecentric stop 34 is, for example, a lens stop for preventing the anterior eye part image from blurring. The pupil and the telecentric stop 34 are conjugated with each other.

The first adjusting optical system 50 is for, for example, mainly performing a working distance adjustment, and includes light source parts 51 and 55, converging lenses 52 and 53, and a light receiving part 54. Here, the working distance adjustment is performed such that, for example, a parallel luminous flux emitted from the light source part 55 and near the optical axis is irradiated to the eye 60 to be examined, and the light reflected by the eye 60 to be examined is received by the light receiving part 54 through the converging lenses 52 and 53. Besides, in the case where the eye 60 to be examined is in a suitable working distance, a spot image from the light source part 55 is formed on the optical axis of the light receiving part 54. On the other hand, in the case where the eye 60 to be examined falls outside the suitable working distance, the spot image from the light source part 55 is formed above or below the optical axis of the light receiving part 54. Incidentally, since the light receiving part 54 has only to detect a change in luminous flux position on a plane including the light source part 55, the optical axis and the light receiving part 54, for example, a one-dimensional CCD disposed on this plane, a position sensing device (PSD) or the like can be applied.

The third illumination optical system 90 includes an optical path for projecting a target for fixation of the eye to be examined or fogging, and includes the third light source part (for example, lamp) 91, a fixation target 92, and a relay lens 93. The fixation target 92 can be irradiated toward the fundus 61 by the luminous flux from the third light source part 91, and the eye 60 to be examined is made to observe it. The fixation target 92 can be made a landscape chart, a circular opening or the like, and the third light source part 91 can be made to emit visible light or near-infrared light, and when the near-infrared light is used, its image can be measured by the second light receiving part 520 of the second reception optical system 300B. The fixation target 92 and the fundus 61 are conjugated with each other.

(Second Embodiment)

Figure 2:
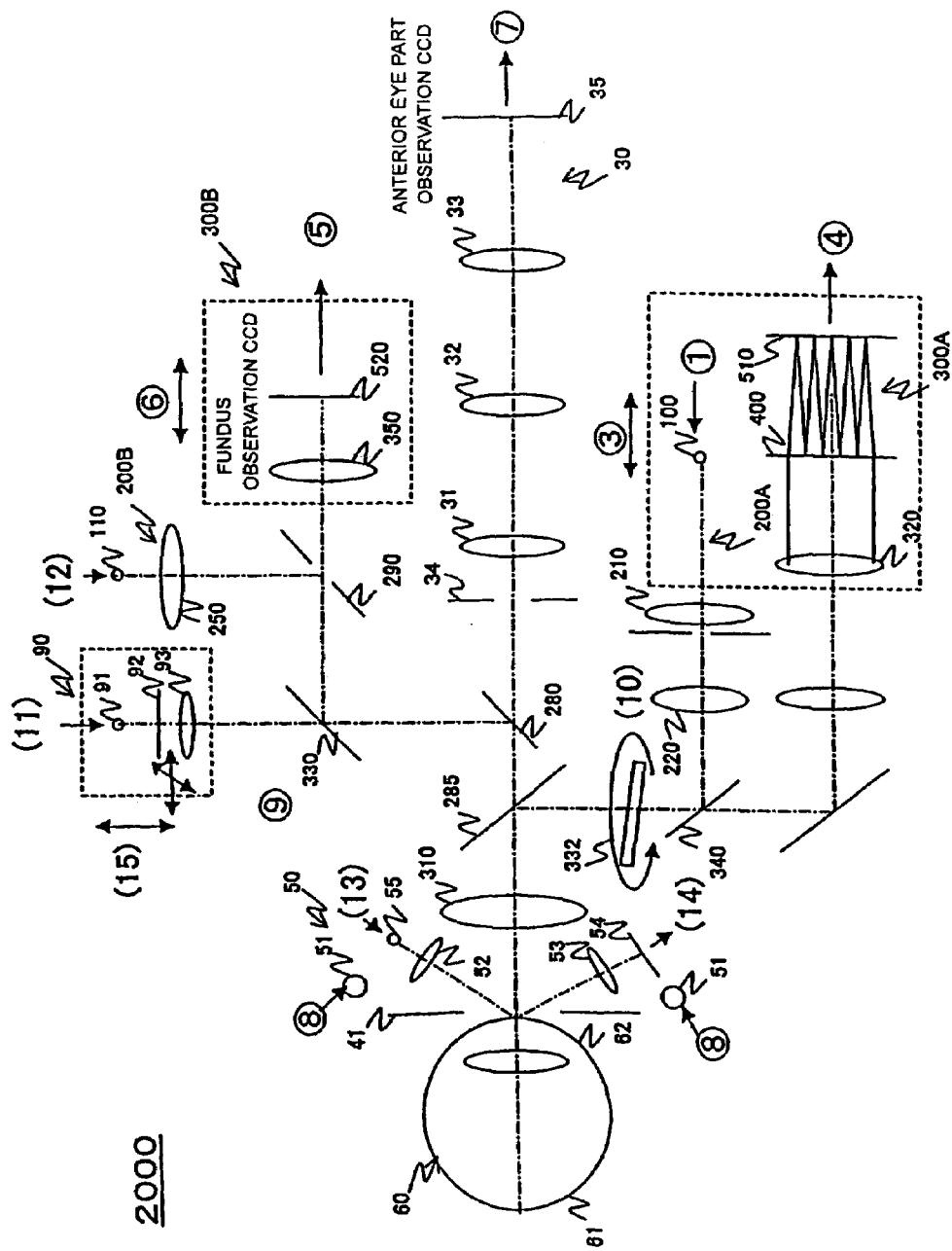
FIG. 2 is a view showing a schematic optical system of an eye characteristic measuring device 2000 of a second embodiment of the invention.

FIG. 2 is a view showing a schematic optical system of an eye characteristic measuring device 2000 of a second embodiment of the invention. Incidentally, blocks and structures overlapping with those of the eye characteristic measuring device 1000 are denoted by the same symbols, and their functions and structures are the same.

In the eye characteristic measuring device 2000, the guidance of an eye 60 to be examined to a specified position can be performed by the movement of a fixation target or the use of a prism. Specifically, in the movement of the fixation target, a fixation target 92 of a third illumination optical system 90 can be moved in a direction orthogonal to an optical axis. Besides, in the use of the prism, the prism is inserted after a relay lens 93, and the optical axis can be moved.

(Third Embodiment)

Figure 3:
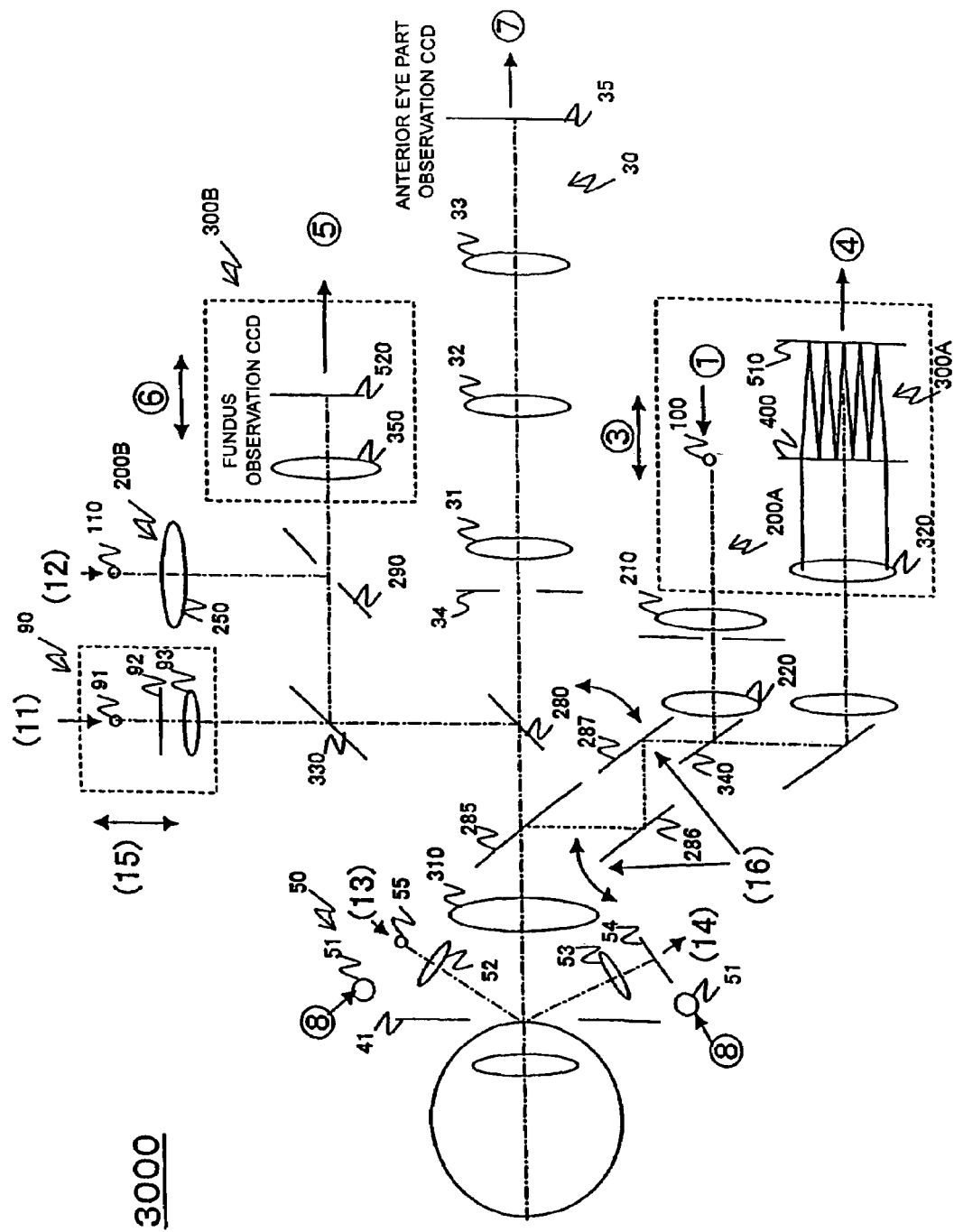
FIG. 3 is a view showing a schematic optical system of an eye characteristic measuring device 300 of a third embodiment of the invention.

FIG. 3 is a view showing a schematic optical system of an eye characteristic measuring device 3000 of a third embodiment of the invention. Incidentally, blocks, structures and the like overlapping with those of the eye characteristic measuring device 1000 are denoted by the same symbols and their functions and structures are the same.

In the eye characteristic measuring device 3000, two galvanometer mirrors 286 and 287 are inserted between a second beam splitter 340 and a beam splitter 285. Here, in the eye characteristic measuring device 3000, in the case where projection light of a conversion member 400 is moved, the galvanometer mirrors 286 and 287 are respectively inclined in an x direction and a y direction to change an incident position. When a desired incident position is obtained, swing is made in a minute angle, and uneven reflection due to disturbance on the retina can be removed.

2. Electric System (First Embodiment)

Figure 4:
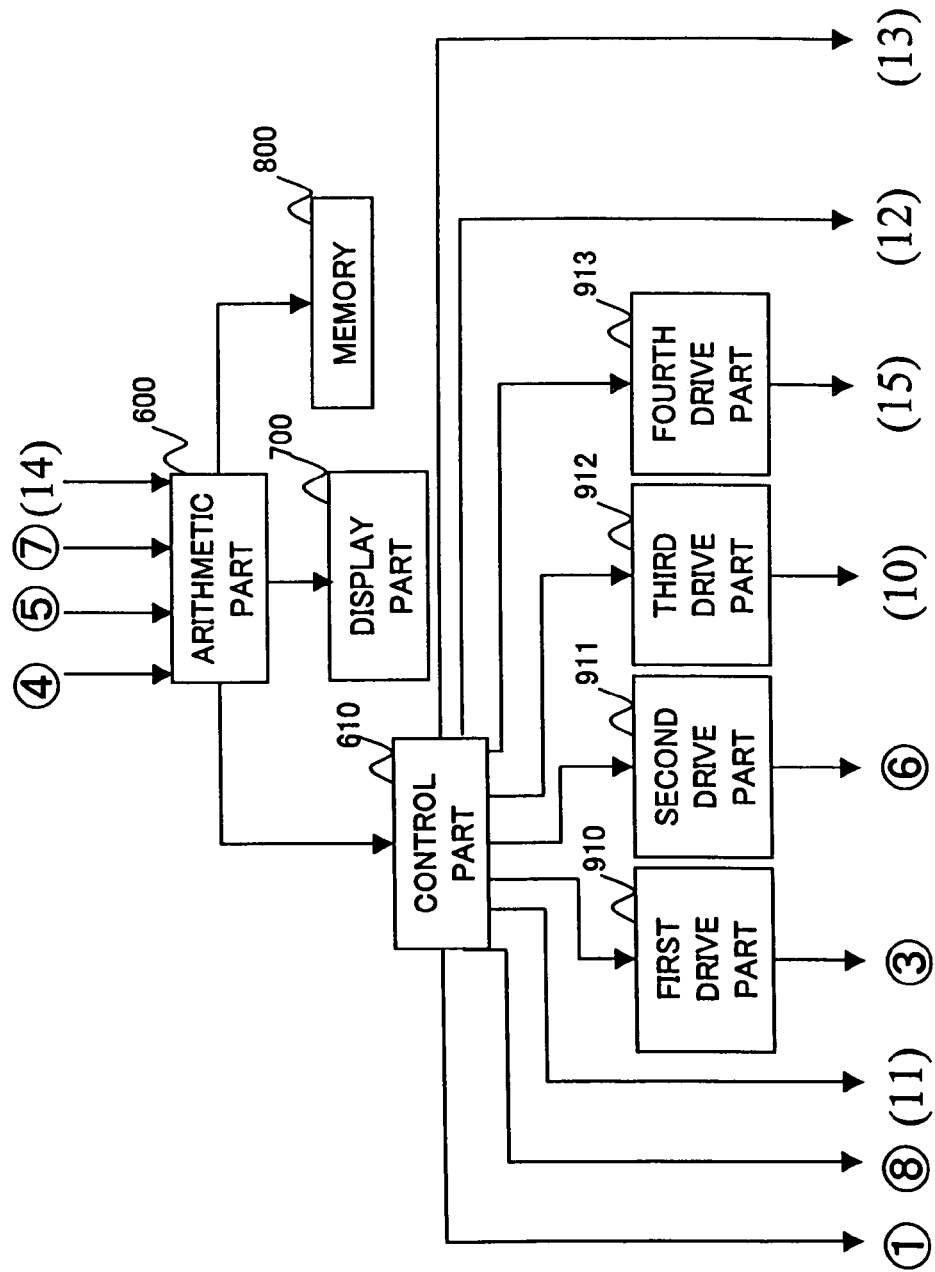
FIG. 4 is an electric system block diagram showing an electric structure of the eye characteristic measuring device 1000 of the first embodiment of the invention.

FIG. 4 is an electric block diagram showing an electric structure of the eye characteristic measuring device 1000 of the first embodiment of the invention.

An electric driving system of the eye characteristic measuring device 1000 includes an arithmetic part 600, a control part 610, a display part 700, a memory 800, a first drive part 910, a second drive part 911, a third drive part 912, and a fourth drive part 913. The arithmetic part 600 includes an imaging state changing part for changing a state at the time when wavefront measurement is performed, and a measurement part for performing various eye characteristic measurements.

Besides, the arithmetic part 600 is constructed such that a first signal ④ from the first light receiving part 510, a second signal ⑤ from the second light receiving part 520, a signal ⑦ from the third light receiving part 35, and a signal (14) from the light receiving part 54 are inputted. The arithmetic part 600 obtains the optical characteristic of the eye 60 to be examined on the basis of the first signal ④ from the first light receiving part 510, and detects the illumination state of the first illumination optical system 200A on the basis of the second signal ⑤ from the second light receiving part 520. Besides, the arithmetic part 600 outputs signals corresponding to the arithmetic results to the control part 610 for controlling the whole of the electric driving system, the display part 700 (various display examples will be described later) and the memory 800.

The arithmetic part 600 obtains, for example, the optical characteristic of the eye 60 to be examined on the basis of the first signal corresponding to the inclination angle of the luminous flux and from the first light receiving part 510, and detects the illumination state of the first illumination optical system 200A on the basis of the second signal from the second light receiving part 520.

The imaging state changing part changes the imaging state of the first illumination optical system 200A and the first reception optical system 300A into the first change state in accordance with the level of the first signal ④ from the first light receiving part 510, and then, changes the imaging state of the first illumination optical system 200A and the first reception optical system 300A into the second change state in accordance with the optical characteristic obtained by the arithmetic part 600. Incidentally, here, although the first wavelength is set to be shorter than the second wavelength, the relation may be inverted.

The control part 610 is for controlling the switching on and off of the first light source part 100 on the basis of the control signal from the arithmetic part 600 and for controlling the first drive part 910 to the fourth drive part 913. The control part 610, on the basis of the signals according to the arithmetic result at the arithmetic part 600, outputs, for example, a signal ① to the first light source part 100, outputs a signal (12) to the second light source part 110, outputs a signal (11) to the third light source part 91, outputs a signal (13) to the light source part 55, outputs a signal ⑧ to the light source part 51, and outputs signals to the first drive part 910 to the fourth drive part 913.

The first drive part 910 is for moving, for example, the first illumination optical system 200A and the first reception optical system 300A in the optical axis direction on the basis of the light receiving signal ④ inputted to the arithmetic part 600 from the first light receiving part 510, outputs a signal ③ to a not-shown suitable lens movement unit, and drives the lens movement unit.

The second drive part 911 is for moving, for example, the second reception optical system 300B in the optical axis direction on the basis of the light receiving signal ⑤ inputted to the arithmetic part 600 from the second light receiving part 520, outputs a signal ⑥ to a not-shown suitable lens movement unit, and drives the lens movement unit.

The third drive part 912 is for rotating, for example, the rotary prism 332, outputs a signal (10) to a not-shown suitable lens movement unit, and drives the lens movement unit.

The fourth drive part 913 is for, for example, moving the third illumination optical system 90, outputs a signal (15) to a not-shown suitable movement unit, and drives the movement unit. By this, the fourth drive part 913 can move and adjust the fixation target 92 of the third illumination optical system 90.

(Second and Third Embodiments)

Incidentally, the eye characteristic measuring device 2000 further includes another drive part which outputs a signal ⑨ to a not-shown suitable movement unit, and drives the movement unit so that the fixation target 92 of the third illumination optical system 90 can be suitably moved in the x direction and the y direction. Besides, the eye characteristic measuring device 3000 further includes another drive part which outputs a signal (16) to a not-shown suitable movement unit and drives the movement unit so that the galvanometer mirrors 286 and 287 can be suitably inclined in the x direction and the y direction.

3. Flowchart (First Embodiment)

Figure 5:
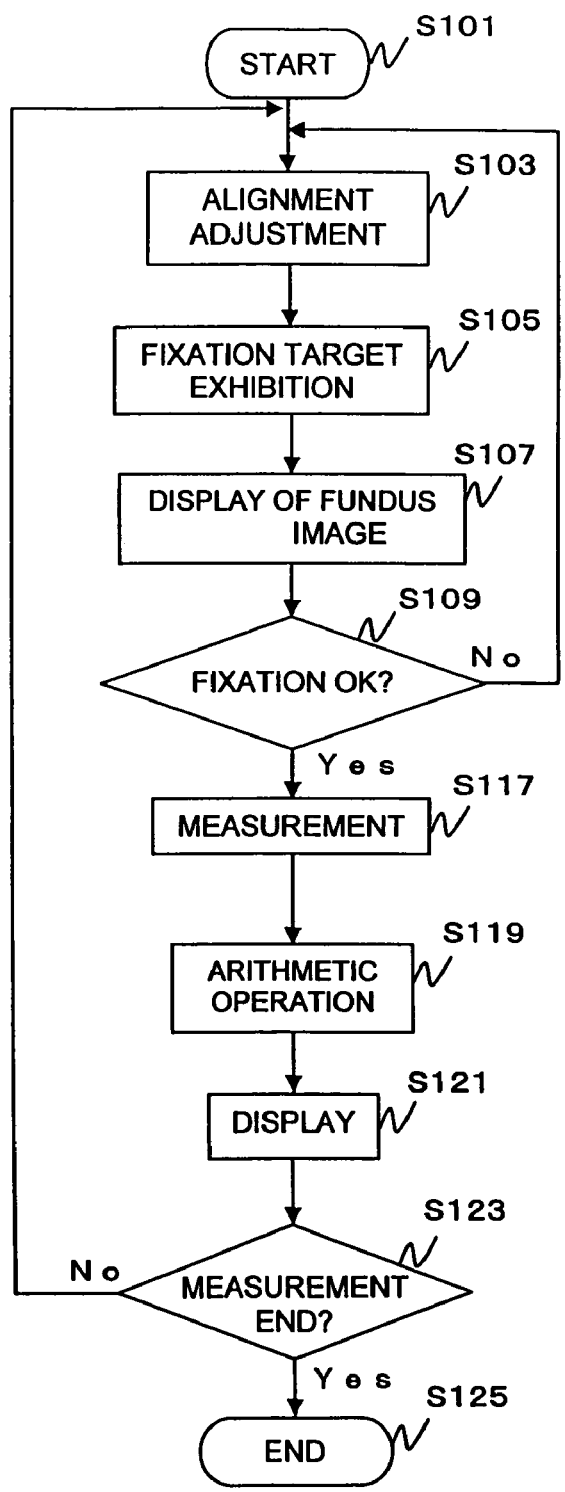
FIG. 5 is a flowchart of the eye characteristic measuring device 1000 of the first embodiment of the invention.

FIG. 5 is a flowchart of the eye characteristic measuring device 1000 of the first embodiment of the invention. Incidentally, the flowchart here is for observing the fixation target at the fundus 61 of the eye 60 to be examined and the irradiation position of light for wavefront sensing using Shack-Hartmann method.

When measurement is started (S101), the alignment adjustment of the position of the eye 60 to be examined is performed (S103). Here, for example, the control part 610 controls a specified drive part on the basis of the control signal from the arithmetic part 600, and moves the optical axis of each of the optical systems to the origin position (S103). Incidentally, with respect to the alignment of the eye characteristic measuring device at the cornea, it is appropriate that illumination is performed by a luminous flux in parallel, a bright point occurs at a position of ½ of a corneal radius, and the alignment is performed by this. By the third light source part 91 and the third illumination optical system 90, the exhibition of the fixation target is performed (S105). By the signal from the second light receiving part 520 of the second reception optical system 300B, the arithmetic part 600 displays a fundus image on the display part 700 (S107).

Here, the fundus image will be described.

Figure 7:
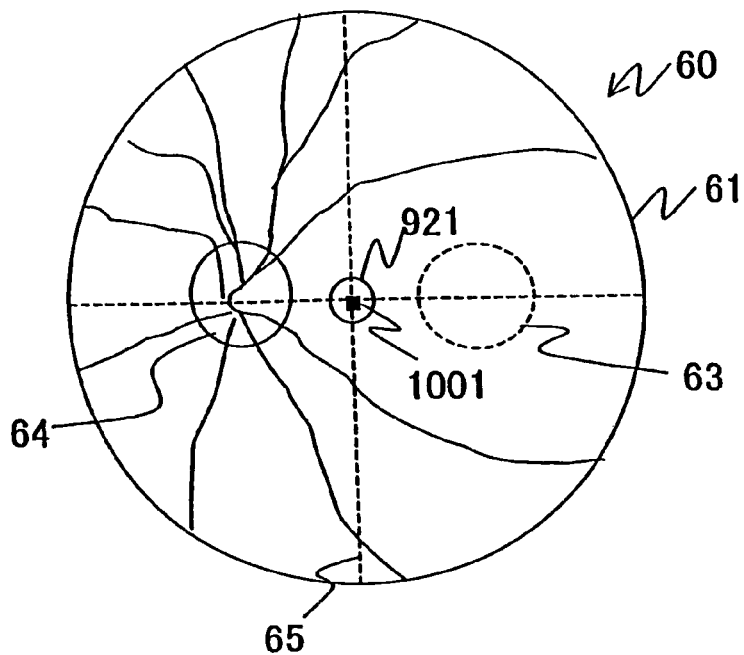
FIG. 7 is a view (1) showing a display example of a fundus image.
Figure 7:
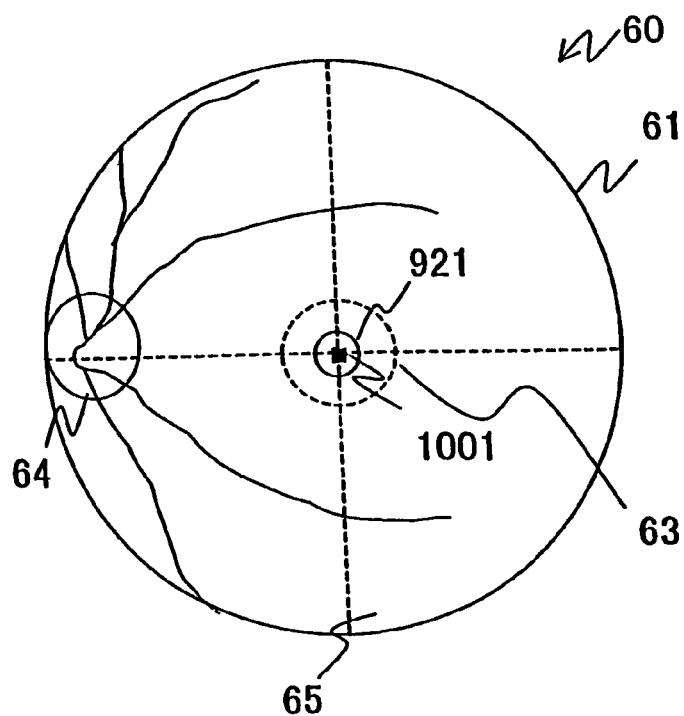

FIG. 7 is a view (1) showing a display example of the fundus image. The fundus 61 is wholly uniformly displayed by the luminous flux from the illumination light source part (here, the second light source part 110) for illuminating the fundus 61. The fundus image includes, in addition to the fundus 61 of the eye 60 to be examined, a macula 63, and an optic disk 64, a fixation target luminous flux 921 (in the drawing, ○) from the third illumination optical system 90 including the third light source part 91 and the fixation target 92, a Center luminous flux of wavefront sensing using Shack-Hartmann method 1001 (in the drawing, ■) showing the center of the incident light of the first light source part 100, and a center line 65 of the second light receiving part 520 as a fundus observation CCD. Besides, in the case where the alignment adjustment is performed at the step S103, the fixation target luminous flux 921 and the Center luminous flux of wavefront sensing using Shack-Hartmann method 1001 are positioned at the center of the center line 65, and are coincident with each other. There is also a case where the fixation target luminous flux 921 is not observed.

Next, it is judged whether or not the macula 63 is displayed at the center (position of the fixation target luminous flux 921, and the Center luminous flux of wavefront sensing using Shack-Hartmann method 1001) of the center line 65 of the fundus image displayed at the step S107 (S109). In the case where the macula 63 is out of the center line 65, a return is made again to the step S103, and the alignment adjustment is performed. In the case where the measurement at the macula 63 is performed, for example, when a subject is instructed to stare at the fixation target luminous flux 921, and the macula 63 is normally moved and comes to include the fixation target luminous flux 921 (in the drawing (b)). Incidentally, a object may perform this judgment by the display part 700, or the arithmetic part 600 may perform the judgment processing by an image processing technique or a pattern recognition technique. Besides, construction can also be made such that the picture image indicating the fundus image at the step S107, especially the picture image of the fundus image at the measurement is stored and is displayed at a later date, together with the measurement result. By doing so, it becomes possible to confirm to which position on the fundus the measurement luminous flux is irradiated when the measurement is made.

After the step S109, the measurement of the optical characteristic of the eye 60 to be examined is performed by the first reception optical system 300A and the first light receiving part 520 (S117), and the arithmetic operation is performed by the arithmetic part 600 (S119) (the details will be described later). Next, the arithmetic part 600 displays the arithmetic result of the step S119 on the display part 700 (S121: described later). Next, it is judged whether or not the measurement is to be ended (S123), and in the case where it is to be ended, the measurement is ended (S125). On the other hand, in the case where the measurement is not ended, a return is made again to the step S103, and the alignment adjustment is performed.

In the above example, the description has been give to the case where the eye to be examined is made to start at the fixation target, and the measurement is performed in the state where the measurement luminous flux is coincident with the macula. However, according to circumstances, there is also a case where even if the the subject is urged to stare the fixation, the macula and the measurement luminous flux do not overlap with each other. At that time, the measurement is performed in the state as it is, and this can be confirmed by the image at the measurement. Besides, as the need arises, the the subject is urged to stare the fixation, and the measurement is made in a natural viewing state, that is, the judgment of the step S109 can also be omitted. Incidentally, in the foregoing, although the description has been given on the assumption that both the luminous flux of the fixation target and the measurement luminous flux can be observed, in the first embodiment, for the purpose of confirmation, it is sufficient if the luminous flux of the fixation target and the measurement luminous flux are coaxial, and one of the luminous flux of the fixation target and the measurement luminous flux can be observed.

(Second Embodiment)

Figure 6:
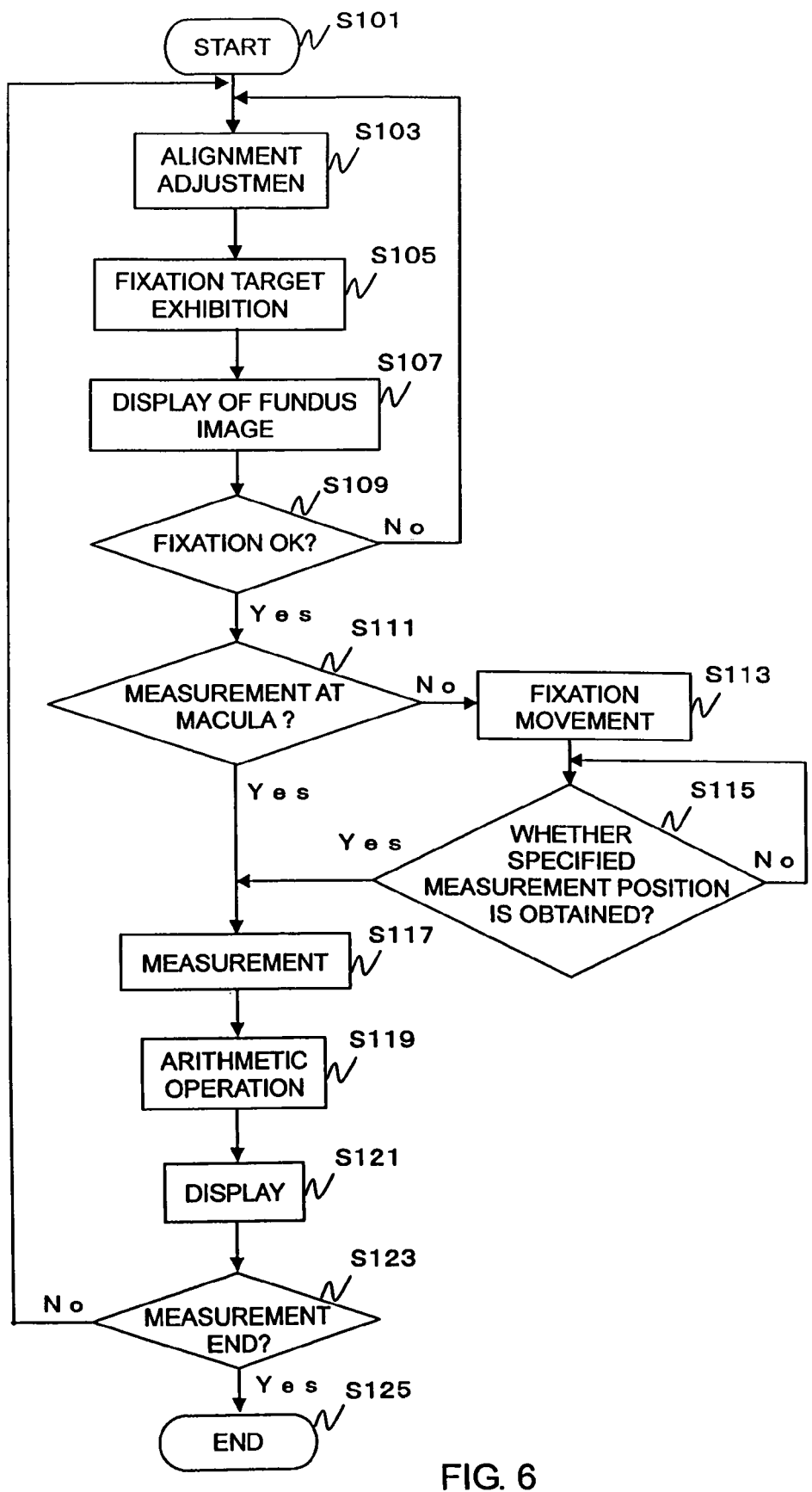
FIG. 6 is a flowchart showing a specific measurement method of the eye characteristic measuring device 2000 of the second embodiment of the invention.

FIG. 6 is a flowchart showing a specific measurement method of the eye characteristic measuring device 2000 of the second embodiment of the invention. Incidentally, processings overlapping with those of the flowchart of the eye characteristic measuring device 1000 are denoted by the same symbols and their functions are the same.

Here, as described above, after the processings of steps S101 to S107 are performed, in the case where the macula 63 is substantially coincident with the center of the center line 65 at step S109 (FIG. 7(*a*)), the arithmetic part 600 judges whether or not the measurement is at the macula 63 by the memory 800 or inputted instructions (S111). Incidentally, a object may previously input the instructions in the memory 800, or may input them at this time.

Here, at the step S111, in the case where the measurement is not at the macula 63 (for example, in the case where the measurement is desired at an intended position of the fundus image), for example, the fixation target luminous flux 921 is moved (step S113). A description will be given to a case where the fixation target luminous flux 921 is moved at the step S113.

Figure 8:
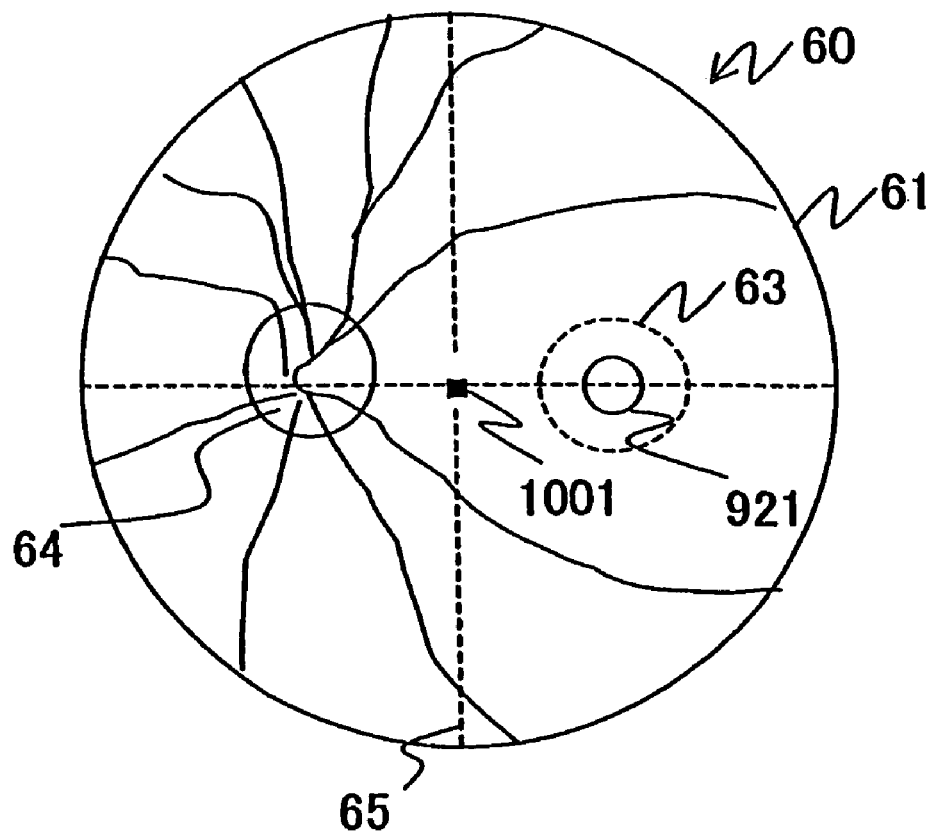
FIG. 8 is a view (2) showing a display example of a fundus image.

FIG. 8 is a view (2) showing a display example of the fundus image.

Here, the second adjustment optical system 90 is driven by the drive part, so that the position of the fixation target 92 is changed, and the fixation target luminous flux 921 is also moved as shown in the drawing. At this time, it is ideal that the macula 63 follows the movement of the fixation target and moves. Thus, for the purpose of confirming the position of the macula 63, it is judged whether or not a specified measurement position (state where the fixation target luminous flux 921 is contained in the macula 63) is obtained (S115). Incidentally, a object may perform this judgment by the display part 700, or the arithmetic part 600 may perform the judgment processing by an image processing technique or a pattern recognition technique. Thereafter, the arithmetic part 600 performs the processings of steps S117 to S125 as described above.

In the foregoing, the description has been given to the case where when the subject is urged to stare the fixation, the fixation target coincides with the macula position. However, according to the eye to be examined, there is also a case where even if the the subject is urged to stare the fixation, the fixation target does not coincide with the macula position. In such a case, when the measurement is desired in a state where the measurement luminous flux is irradiated to the macula, it is also possible to make the measurement center luminous flux 1001 coincident with the macula by moving the fixation target luminous flux 921.

(Third Embodiment)

Next, a flowchart of the eye characteristic measuring device 3000 of the third embodiment will be described. As the flowchart showing its specific measurement method, at the step S113 in the second embodiment, instead of moving the fixation target luminous flux 921, the foregoing galvanometer mirrors 286 and 287 are inclined, and the Center luminous flux of wavefront sensing using Shack-Hartmann method 1001 is moved.

A description will be given to a case where the Center luminous flux of wavefront sensing using Shack-Hartmann method 1001 is moved at the step S113.

Figure 9:
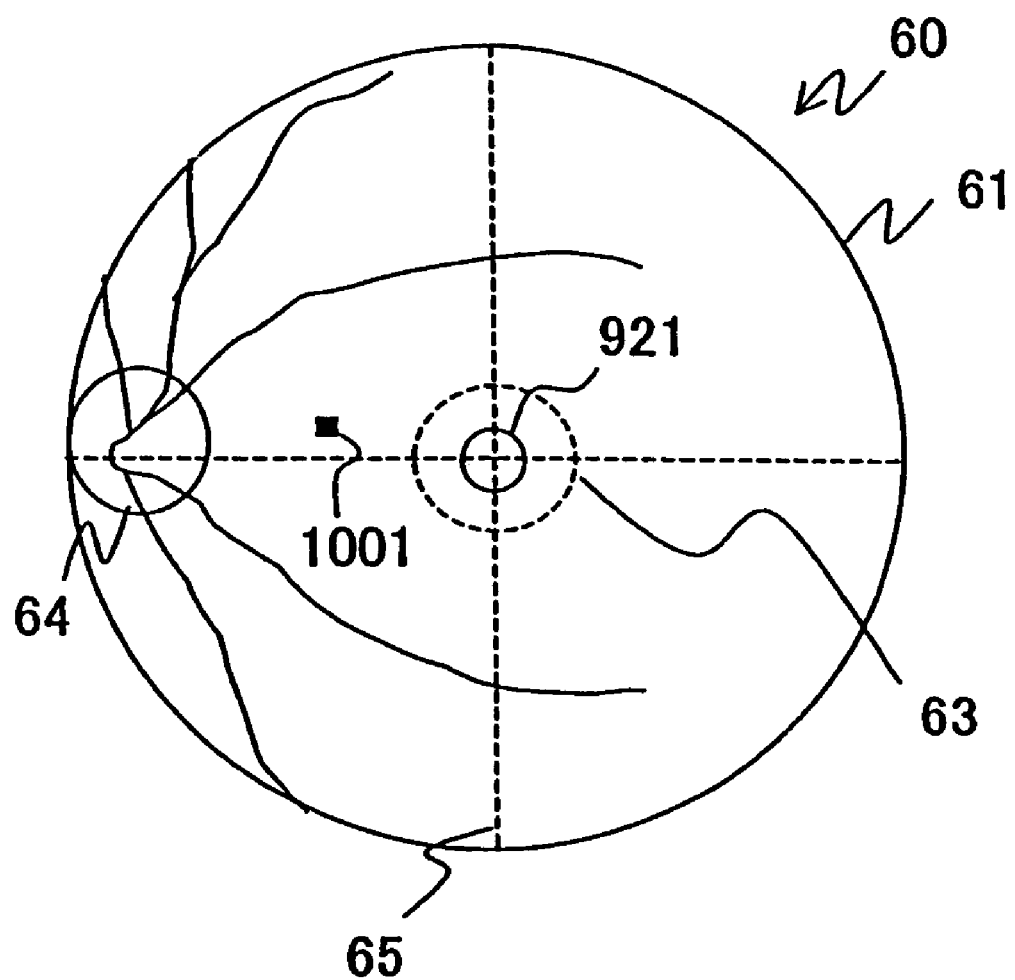
FIG. 9 is a view (3) showing a display example of a fundus image.

FIG. 9 is a view (3) showing a display example of the fundus image.

Here, the first illumination optical system 200A is driven by the first drive part 910, or the galvanometer mirrors 286 and 287 are driven by the first drive part or the driving means (16), so that the position of the Center luminous flux of wavefront sensing using Shack-Hartmann method 1001 is changed, and the Center luminous flux of wavefront sensing using Shack-Hartmann method 1001 is also moved as shown in the drawing. At this time, for the purpose of confirming the position of the Center luminous flux of wavefront sensing using Shack-Hartmann method 1001 and the macula 63, it is judged whether or not a specified measurement position (state in which the fixation target luminous flux 921 is contained in the macula 63, and the Center luminous flux of wavefront sensing using Shack-Hartmann method 1001 does not coincide with the fixation target luminous flux 921) is obtained (S115). Thereafter, the arithmetic part 600 performs the processings of steps S117 to S125 as described above.

In the foregoing, the description has been given to the case where when the subject is urged to stare the fixation, the fixation target coincides with the macula position. However, according to the eye to be examined, even if the the subject is urged to stare the fixation, there is also a case where the fixation target does not coincide with the macula position.

In such a case, when the measurement is desired in a state where the measurement luminous flux is irradiated to the macula, this can be used in moving the measurement center luminous flux 1001 so that it coincides with the macula.

4. Beam Splitter

Figure 10:
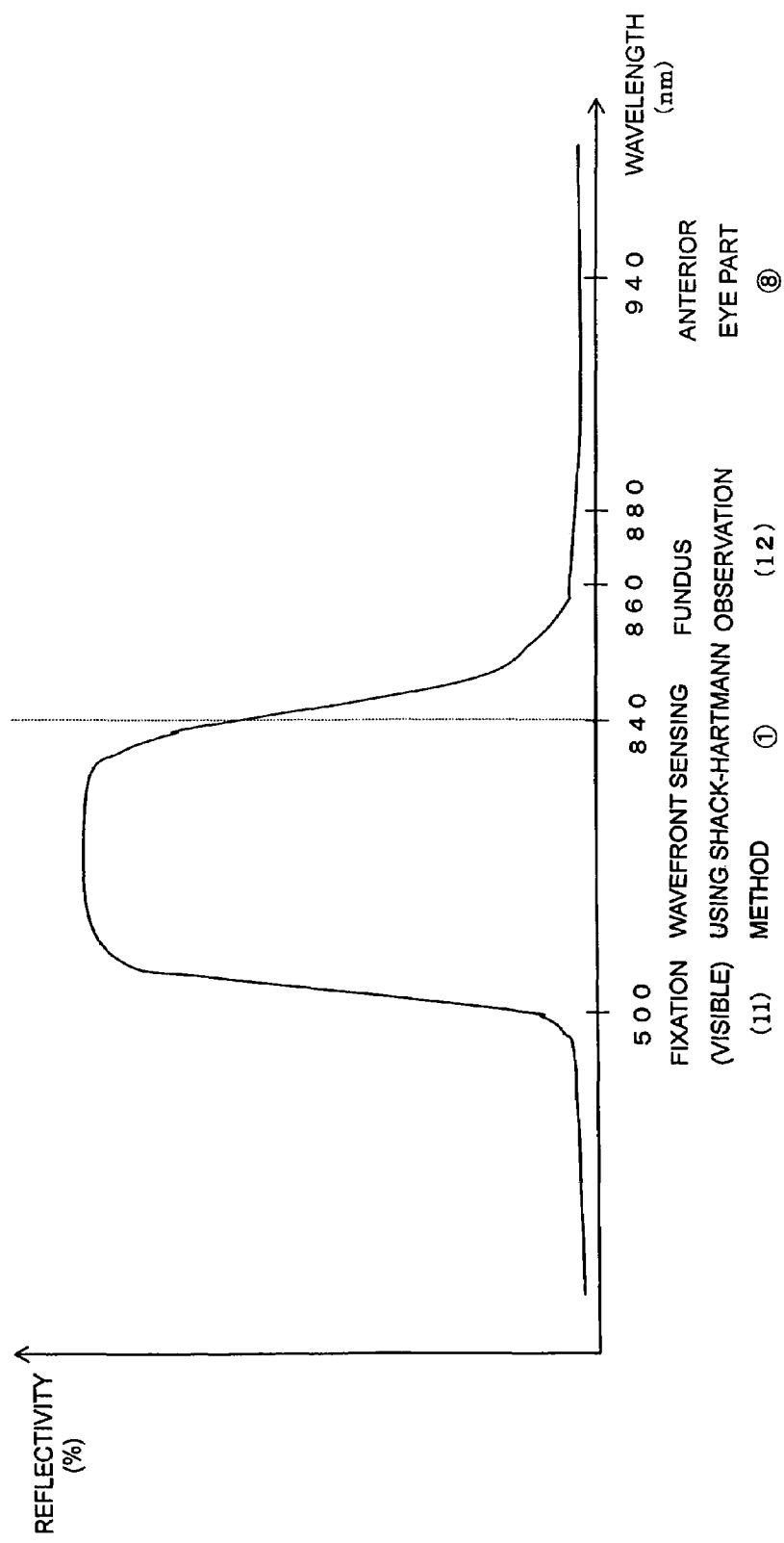
FIG. 10 is a view showing an example of a characteristic view of a beam splitter.

FIG. 10 shows an example of a characteristic view of a beam splitter.

The characteristic of the beam splitter 285 can be made the characteristic as shown in the drawing. The characteristic as the band pass filter is such that most of the wavefront luminous flux is reflected, and apart thereof is transmitted (for example, 5% of the flux is transmitted, and 95% thereof is reflected), and most of the fundus illumination luminous flux and the fixation target luminous flux are transmitted. Here, as an example, the wavelength of the first light source part 100 for wavefront luminous flux is 840 nm, the wavelength of the second light source part 110 for fundus illumination luminous flux is 860 to 880 nm, the wavelength of the third light source part 91 for fixation target luminous flux is 500 nm, and the wavelength of the light source part 51 for anterior eye part observation is 940 nm, however, no limitation is made to these.

Besides, as a modified example of the optical system, when construction is made such that separation is performed in ascending order of wavelength, the construction can be made by only high-pass filters (fixation target luminous flux, wavefront measurement luminous flux, fundus observation luminous flux, and anterior eye part illumination). Besides, when construction is made such that separation is performed in descending order of wavelength, the construction can be made by only low-pass filters (anterior eye part illumination, fundus observation luminous flux, wave front measurement luminous flux, and fixation target luminous flux).

5. Display Example

Figure 11:
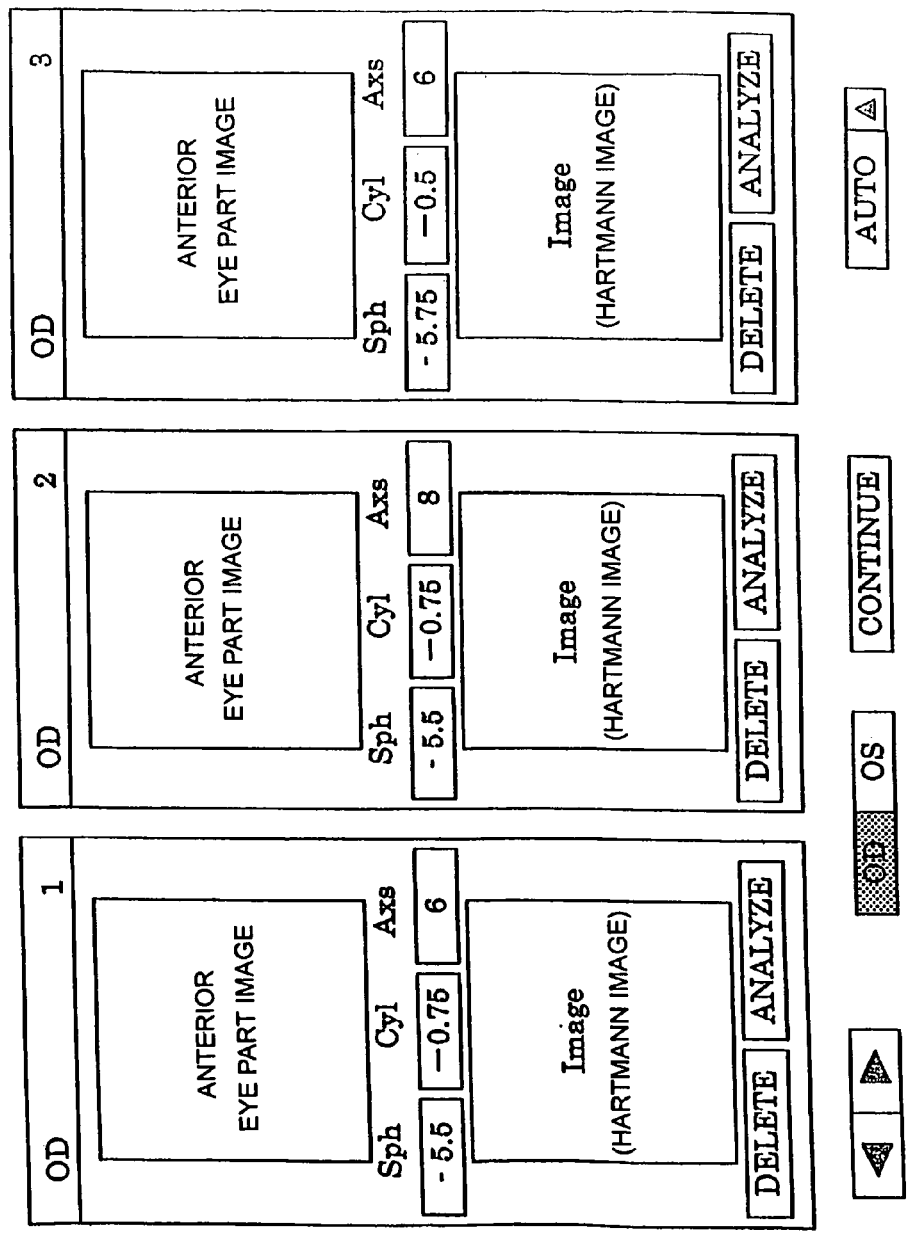
FIG. 11 is an explanatory view showing a display example graphic displayed on a display part 700.

FIG. 11 is an explanatory view showing a display example of a graphic display on the display part 700.

Here, there is shown a state in which a first, a second and a third displays of measurement results are respectively performed on the display part 700 (for example, a display of a personal computer, etc.). On the display part 700, for example, the anterior eye part image, the Hartmann image, and values of (S, C, Ax) as measurement results of refractive measurement are displayed.

"AUTO" in the drawing is a mode setting button for deciding an exposure time automatically or manually. That is, when a proper user operates this mode setting button, for example, in the case where setting of the exposure time goes wrong, or in the case where measurement with different light quantity and exposure time is desired, the manual setting can be performed. At this time, the exposure time may be directly inputted, or levels are previously determined to a certain degree and a level may be selected among them.

6. Measurement of Optical Characteristic

Next, the measurement of the optical characteristic at the steps S117 and S119 of the foregoing flowchart will be described in detail.

Figure 12:
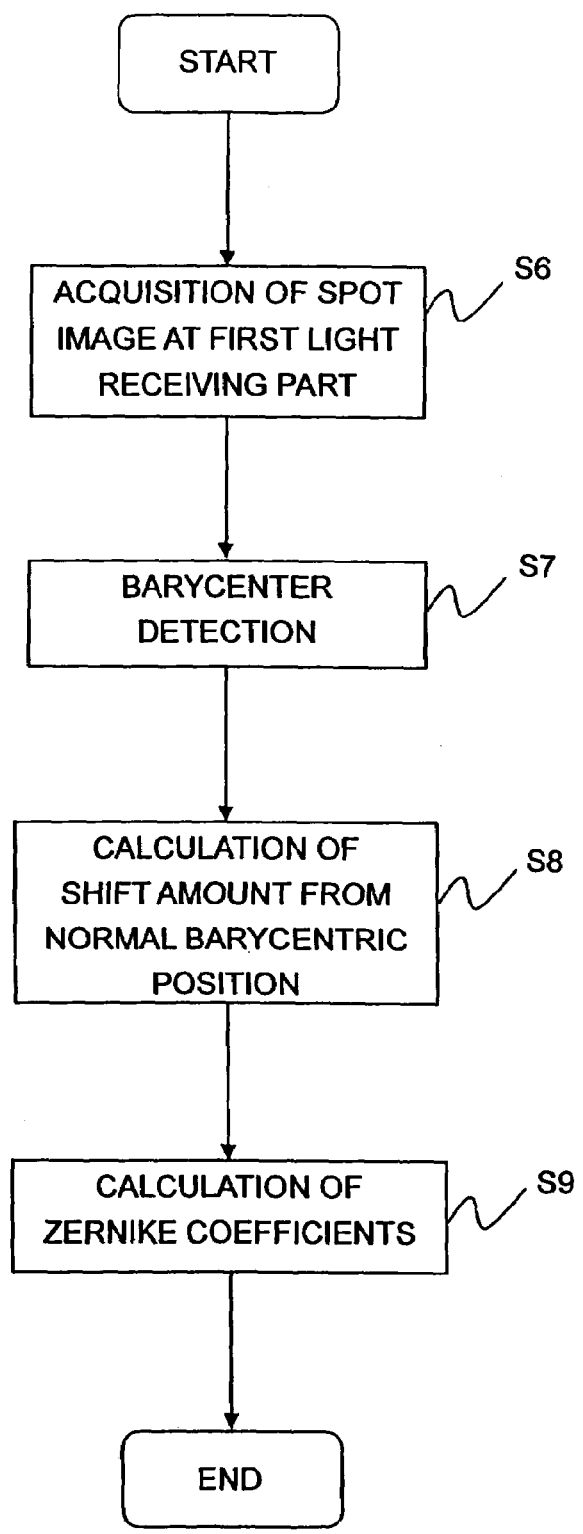
FIG. 12 is a flowchart concerning Wavefront sensing using Shack-Hartmann method.

FIG. 12 is a flowchart concerning Wavefront sensing using Shack-Hartmann method.

Specifically, for example, spot images are taken by the first light receiving part 510 (S6), and further, the barycentric position of each of the spots is detected (S7). With respect to this barycentric position, for example, a projected luminous flux is made to be projected on plural pixels on the light receiving plane, and the barycentric position can also be obtained by referring to the intensity of the luminous flux of each of the pixels. By calculating the barycenter as stated above, measurement position accuracy of $1/10$ or less of the element can be ensured. Next, the amount of shift from a barycentric position of emmetropia is calculated (S8). Further, Zernike coefficients are calculated (see JP-A-2001-204690) (S9).

INDUSTRIAL APPLICABILITY

According to the present invention, as described above, it becomes possible to confirm at which position on the fundus of the eye to be examined the luminous flux for measurement is converged or fixed, and further, the fixation target or the irradiation position of irradiation light for wavefront sensing using Shack-Hartmann method is moved, so that the converging position and the measurement position can be changed, and the reliability of data can be further raised.

The invention claimed is:

1. A device for measuring an optical characteristic of an eye, comprising:
   a first light source for emitting a luminous flux of a first wavelength;
   a first illumination optical system for performing illumination by a first illumination luminous flux which is from the first light source and is converged to a vicinity of a center of a fundus of an eye to be examined;
   a second light source for emitting a luminous flux of a second wavelength;
   a second illumination optical system for illuminating an observation area of the fundus of the eye to be examined by a second illumination luminous flux from the second light source;
   a beam splitter for branching a reflected luminous flux reflected from the fundus of the eye to be examined into a first branch luminous flux containing most of the reflected luminous flux of the first wavelength and a second branch luminous flux containing a remaining portion of the reflected luminous flux of the first wavelength and the reflected luminous flux of the second wavelength;

a first reception optical system for receiving the first branch luminous flux branched by the beam splitter and for guiding the first branch luminous flux so as to be received through a first conversion member for converting it into at least 17 beams;

a first light receiving part for receiving the first branch luminous flux from the first reception optical system;

a second reception optical system for guiding the second branch luminous flux branched by the beam splitter so as to be received;

a second light receiving part for receiving the second branch luminous flux from the second reception optical system;

an arithmetic part for obtaining the optical characteristic of the eye to be examined on the basis of an inclination angle of the luminous flux obtained by the first light receiving part; and a display part for enabling confirmation of an irradiation position of the first illumination luminous flux on the fundus by a signal from the second light receiving part.

2. A device for measuring an optical characteristic of an eye according to claim 1, further comprising a fixation target projection optical system which includes a fixation target for forming a fixation target image on the fundus of the eye to be examined, enables a fixation target position to be moved in a direction orthogonal to an optical axis, and is for instructing to change a converging position of the first illumination luminous flux on the fundus of the eye to be examined by movement of the fixation target.

3. A device for measuring an optical characteristic of an eye according to claim 1, further comprising a fixation target projection optical system which includes a fixation target for forming a fixation target image on the fundus of the eye to be examined, and a reflecting mirror having rotation axes in directions substantially orthogonal to each other in a vicinity of an imaging position of the fixation target, and is constructed to change a converging position of the first luminous flux on the fundus of the eye to be examined by movement of the mirror.

4. A device for measuring an optical characteristic of an eye according to claim 1, wherein the first illumination optical system includes a luminous flux direction conversion member, and a converging position of the first luminous flux on the fundus of the eye to be examined is changed by a change in a luminous flux direction.

5. A device for measuring an optical characteristic of an eye according to claim 1, wherein the second light source part is a surface light source or a point light source having a wavelength of 860 to 880 nm.

6. A device for measuring an optical characteristic of an eye according to claim 1, wherein the arithmetic part judges whether a position of a fixation target image is near a position of a macula.

7. A device for measuring an optical characteristic of an eye according to claim 2, wherein the second light source part is a surface light source or a point light source having a wavelength of 860 to 880 nm.

8. A device for measuring an optical characteristic of an eye according to claim 3, wherein the second light source part is a surface light source or a point light source having a wavelength of 860 to 880 nm.

9. A device for measuring an optical characteristic of an eye according to claim 4, wherein the second light source part is a surface light source or a point light source having a wavelength of 860 to 880 nm.

10. A device for measuring an optical characteristic of an eye according to claim 2, wherein the arithmetic part judges whether a position of a fixation target image is near a position of a macula.

11. A device for measuring an optical characteristic of an eye according to claim 3, wherein the arithmetic part judges whether a position of a fixation target image is near a position of a macula.

12. A device for measuring an optical characteristic of an eye according to claim 4, wherein the arithmetic part judges whether a position of a fixation target image is near a position of a macula.

13. A device for measuring an optical characteristic of an eye according to claim 5, wherein the arithmetic part judges whether a position of a fixation target image is near a position of a macula.

* * * * *